United States Patent
Chen et al.

(10) Patent No.: US 11,547,702 B2
(45) Date of Patent: Jan. 10, 2023

(54) USE OF AMLEXANOX

(71) Applicant: SHANGHAI MICROPORT MEDICAL (GROUP) CO., LTD., Shanghai (CN)

(72) Inventors: Lu Chen, Shanghai (CN); Junfei Li, Shanghai (CN); Fei Chen, Shanghai (CN); Xiao Cheng, Shanghai (CN)

(73) Assignee: MICROPORT SINICA CO., LTD., Shanghai (CN)

( * ) Notice: Subject to any disclaimer, the term of this patent is extended or adjusted under 35 U.S.C. 154(b) by 0 days.

(21) Appl. No.: 16/337,357

(22) PCT Filed: Sep. 7, 2017

(86) PCT No.: PCT/CN2017/100885
§ 371 (c)(1),
(2) Date: Mar. 27, 2019

(87) PCT Pub. No.: WO2018/059207
PCT Pub. Date: Apr. 5, 2018

(65) Prior Publication Data
US 2020/0038380 A1  Feb. 6, 2020

(30) Foreign Application Priority Data
Sep. 27, 2016 (CN) .......................... 201610855771.8

(51) Int. Cl.
A61K 31/436 (2006.01)
A61K 45/06 (2006.01)
A61L 31/16 (2006.01)

(52) U.S. Cl.
CPC ............ *A61K 31/436* (2013.01); *A61L 31/16* (2013.01); *A61K 45/06* (2013.01)

(58) Field of Classification Search
CPC ....... A61K 31/416; A61K 45/06; A61L 31/16; A61L 33/0005
See application file for complete search history.

(56) References Cited

U.S. PATENT DOCUMENTS

| | | | | |
|---|---|---|---|---|
| 5,362,737 A | * | 11/1994 | Vora ................. | A61K 8/49 424/54 |
| 2005/0100654 A1 | * | 5/2005 | Su ..................... | B05D 1/42 427/2.1 |
| 2007/0179596 A1 | * | 8/2007 | Davila ............... | A61L 27/34 623/1.42 |

FOREIGN PATENT DOCUMENTS

| | | |
|---|---|---|
| CN | 102137642 A | 7/2011 |
| EP | 2243501 A1 | 4/2009 |
| JP | 2005504060 A | 2/2005 |
| JP | 2010159268 A | 7/2010 |
| WO | WO03/018595 A2 | 3/2003 |
| WO | WO 2009/007673 A2 | 1/2009 |

OTHER PUBLICATIONS

Landriscina et al, The Journal of Biological Chemistry (2000), vol. 275(42), pp. 32753-32762. (Year: 2000).*
Watanabe et al., "Changes in isolated ciliary muscle caused by repeated instillation of carbachol ointment in rabbits and efffect of topically applied amlexanox," Journal of Japanese Ophthalmological Society, vol. 104, Issue 1, pp. 17-23.
Miyazawa et al., "Effects of pemirolast and tranilast on intimal thickening after arterial injury in the rat," Journal of Cardiovascular Pharmacology, vol. 30, No. 2, Jul. 31, 1997, pp. 157-162.
Fu et at., "Amlexanox is as effective as dexamethasone in topical treatment of erosive oral lichen planus: a short-term pilot study," Science Direct, vol. 113, Issue 5, May 2012, pp. 638-643.
Landriscina et al., "Amlexanox reversibly inhibits cell migration and proliferation and induces the Src-dependent dissasembly of Actin Stress Fibers in vitro," J. Biological Chemistry, Vo. 275, No. 42, Oct. 20, 2020, pp. 32753-37262.
Shishibori et al., "Three distinct anti-allergic drugs, amlexanox, cromolyn and tranilast, bind to S100A12 and S100A13 of the S100 protein family," J. Biochemical Society, Vo. 338, 1999, pp. 583-589.
Watanabe et al., "Inhibitory Effects of Amlexanox on Carbachol-induced Contractions of Rabbit Ciliary Muscle and Guinea-pit Taenia Caecum," J. Pharm. Pharmacol, vol. 52, 2000, pp. 1377-1385.
International Search Report and Written Opinion (with English translations) dated Dec. 13, 2017 issued in corresponding Application No. PCT/CN2017/100885.

* cited by examiner

*Primary Examiner* — Craig D Ricci
*Assistant Examiner* — Janet L Coppins
(74) *Attorney, Agent, or Firm* — Muncy, Geissler, Olds & Lowe, P.C.

(57) ABSTRACT

Disclosed is use of amlexanox or a salt thereof or a solvate thereof in preparation of a drug having an inhibitory action on the smooth muscle cells, in particular a drug for preventing and treating vascular restenosis. Further disclosed is a medical device, particularly a drug stent, the surface of which is distributed with amlexanox or the salt thereof or the pharmaceutical composition thereof. Amlexanox has an activity in inhibition of the proliferation of smooth muscle cells, has a low inhibitory property of the endothelial cell growth, is particularly suitable for applying on a medical device to prevent the incidence of vascular restenosis, while not delaying the repair of endothelium.

1 Claim, No Drawings

USE OF AMLEXANOX

CROSS-REFERENCE TO RELATED APPLICATION

The application claims the benefit of priority of Chinese Patent Application No. 201610855771.8, filed on Sep. 27, 2016, and the entire disclosures of which are incorporated herein.

TECHNICAL FIELD

The present invention relates to use of amlexanox or a salt thereof or a solvate thereof in preparation of a drug having an inhibitory action on smooth muscle cells, and in particular, to the use of drugs for preventing and treating vascular restenosis.

The present invention further relates to the technical field of medical instruments.

BACKGROUND

The general name of amlexanox is 2-amimo-7-isopropyl-5-oxo-5H-[1]benzopyrano-[2,3,-b]pyridine-3-carboxylic acid, also known as CHX3673. The chemical name in English is 2-amimo-7-isopropyl-5-oxo-5H-[1]benzopyrano-[2,3,-b]pyridine-3-carboxylic acid. Amlexanox is an allergic mediator blocker, which inhibits the degranulation of mast cells by stabilizing their membranes, so as to prevent the release of allergic mediators and thus has an anti-allergic effect. Amlexanox is first marketed in Japan in 1987 for the treatment of allergic bronchial asthma, and later applied to allergic rhinitis. Amlexanox is approved by the U.S. Food and Drug Administration (FDA) in 1996 for the treatment of oral ulcers.

Amlexanox is the only prescription drug approved by the FDA for the treatment of Aphthous ulcers, and its pharmacological action is mainly accelerating the healing of Aphthous ulcers by anti-allergy and anti-inflammatory action.

In vitro studies have demonstrated that amlexanox is able to strongly inhibit the formation and release of inflammatory mediators (histamines, leukotrienes) from mast cells, neutrophile leucocytes and monocytes. Animal experiments have demonstrated that amlexanox has anti-allergic and anti-inflammatory effects. In vitro studies have shown that 5% amlexanox oral paste has a significant therapeutic effect on experimental oral ulcer of rats induced by 10% acetic acid and experimental oral ulcer of rabbits induced by 90% carbolic acid, which is able to shorten the mean healing time of ulcer surface. Compared with the model group, the healing time is advanced by 2.5 days and 1.75 days, respectively.

From the current clinical use, amlexanox is mainly used to treat allergies and oral ulcers.

Currently, cardiovascular disease is the most serious threat to human health. According to WHO's statistics, the number of deaths due to the cardiovascular disease each year is up to 30% of the total global deaths. Treating the cardiovascular disease with cardiovascular interventional surgery is a trend of clinical development. However, for traditional interventional instruments, such as stents, balloons, occluders, and interventional valves, thrombosis and neoplasms may be formed after interventional surgery, and then Restenosis (RS) may occur, reducing the expected effect of surgery.

Vascular endothelial dysfunction and excessive proliferation/migration of Vascular Smooth Muscle Cells (VSMCs) are important factors in the occurrence of RS. A large number of studies have demonstrated that the proliferation/migration of VSMCs from the tunica media of artery to the intima of artery is a key link of the development and ultimate formation of RS. If the vascular wall is damaged by the balloon or stent, the phenotype of the VSMCs in the tunica media of artery changes (from a resting/contracted state to a proliferative/synthetic phenotype), and the VSMCs increasingly proliferate and migrate to the intima, and over-synthesize and secrete a large number of extracellular matrices, which results in neointima formation of the blood vessel and thus results in restenosis.

Clinically, there is still a certain proportion of restenosis after Drug-Eluting Stent (DES) implantation. Endothelial dysfunction after Percutaneous Coronary Intervention (PCI) can progress to atheromatous plaque lesions, and causes in-stent RS. Factors such as senescence of smooth muscle cells, delayed endothelialization, endothelial phenotypic changes, and stent malapposition may delay endothelialization. Reassessing the pathogenesis of RS, the current drug anti-RS is at the expense of vascular endothelial injury or delayed repair. Maintaining the integrity of the vascular endothelial structure and function plays an important role in reducing stent thrombosis and stent restenosis after PCI. For a more ideal coronary stent system, in addition to the stent itself has good biocompatibility, radial strength and the ability to pass through lesions, the implanted stent should be coordinated with the "internal environment" of the coronary artery to maintain normal endothelialization, intact endothelial function, normal systolic and diastolic function of the coronary artery at the implanted location of the stent, and the structural integrity and normal remodeling of the blood vessels.

At present, DES loaded with proliferation inhibitors (rapamycin and its analogs, paclitaxel) of the smooth muscle cells is the most commonly used treatment for clinical prevention of restenosis. Although the application of DES effectively reduces the incidence of restenosis in a short time after surgery, studies have shown that DES inhibits the proliferation of VSMCs as well as delays endothelial repair, which results in incomplete intimalization of the stent, thrombosis and other cardiovascular diseases, and ultimately weakens the long-term effect of anti-restenosis.

SUMMARY OF THE INVENTION

The inventors of the present invention have surprisingly found that amlexanox is able to inhibit the biological activity of proliferation of vascular smooth muscle cells without inhibiting the growth of the endothelial cells. That is, amlexanox has a selective inhibitory effect, thereby preventing vascular restenosis after PCI.

The present invention relates to use of amlexanox or a salt thereof or a solvate thereof in preparation of a drug having a smooth muscle cell inhibitory effect.

The amlexanox salt in the present invention refers to a pharmaceutically acceptable acid or base addition salt formed by amlexanox and a wide variety of acids or bases, and includes physiologically acceptable salts which are commonly used in the pharmaceutical industry.

The acid and base are organic acids or bases, and may also be inorganic acids or bases.

Further, the drug is a drug for preventing and treating vascular restenosis. Since amlexanox inhibits the proliferation of smooth muscle cells without inhibiting the growth of endothelial cells, it is beneficial to the healing of injured blood vessels and prevents the formation of thrombosis, enabling to shorten the time for patients to take antithrombotic and platelet drugs after surgery.

According to the present invention, the vascular restenosis refers to a condition of recurrence of symptoms at a target lesion or a restenosis of a blood vessel inner diameter after a patient undergoes an interventional surgery.

Further, the drug is prepared into an oral administration dosage form, an injection administration dosage form, a respiratory administration dosage form, a mucosal administration dosage form, a transdermal administration dosage form or a cavitary administration dosage form.

Further, the drug is in a form of tablet, powder, capsule, granule, solution, emulsion, spray, patch or gel.

Pharmaceutical preparations can be obtained by methods known in the art.

The solution pharmaceutical and emulsion pharmaceutical may be prepared as an oral liquid convenient for oral administration, as an injection fitting for intramuscular, subcutaneous or intravenous administration, as an external coating suitable for external application, or as a coating applied to the surface of the medical instrument for topical administration.

The powder may be administered orally or topically administered into the body by a medical instrument.

The present invention further provides a medical instrument, comprising a substrate and an active substance or a pharmaceutical composition distributed on a surface of the substrate, wherein the active substance is amlexanox or a salt thereof, and the pharmaceutical composition comprises amlexanox or a salt thereof.

Further, the pharmaceutical composition further comprises one or more of an immunosuppressive drug, an anti-inflammatory drug, an anti-proliferative drug, a re-endothelialization promoting drug, an anti-cell migration drug, an intercellular matrix regulator drug, and other extracellular matrix proteins.

Further, the pharmaceutical composition consists of the amlexanox or the salt thereof and the anti-proliferative drug.

Further, the drug-loading mass ratio of the amlexanox to the anti-proliferative drug is (1:10)-(10:1), preferably (1:3)-(3:1), and most preferably (1:2.5)-(1.5:1).

Further, the anti-proliferative drug is one or more selected from the group consisting of everolimus, tacrolimus, ridaforolimus, temsirolimus, zotarolimus, irolimus, immunosuppressant ABT-578, dexamethasone, mizoribine, rapamycin, paclitaxel and derivatives thereof, actinomycin, vincristine and derivatives thereof, statins, 2-chlorodeoxyadenosine, ribozyme, batimastat, halofuginone, and probucol, preferably rapamycin and derivatives thereof, namely one or more of everolimus, tacrolimus, ridaforolimus, temsirolimus, zotarolimus, and rapamycin.

Further, the medical instrument is one selected from the group consisting of cardiac valve, cardiac occluder, vascular stent, artificial blood vessel, catheter, pacemaker, pacemaker derivation, and defibrillator, or combinations thereof.

The substrate material may be a metal material or a polymer material which are commonly used in medical instruments.

The metal material may be a degradable or non-degradable metal material. The non-degradable material may be titanium, cobalt, tantalum, nickel-titanium alloy, nickel-titanium-niobium alloy, medical stainless steel, etc. The degradable alloy material is for example aluminum-magnesium alloy, so that complete biological degradation and absorption are able to be achieved.

The polymer material can also be classified into degradable or non-degradable materials, where the degradable material may be Polycaprolactone (PCL), Polyglycolic Acid (PGA), Poly-L-Lactic Acid (PLLA), Polycaprolactone Monoacrylate (PCLA), Polylactic Acid-Glycolic Acid (PLGA) copolymer, and the like.

The drug or the pharmaceutical composition may be distributed on the surface of the medical instrument through a pharmaceutical carrier or may be distributed on the surface of the medical instrument without a carrier.

The drug or pharmaceutical composition is immobilized in the pharmaceutical carrier through physical dispersion, electrostatic adsorption or chemical bonding.

The material of the pharmaceutical carrier can be classified into the material of organic or inorganic, biodegradable or non-biodegradable, as well as synthetic or natural. The organic carrier material mainly refers to a polymer material, and the inorganic carrier material mainly refers to a porous inorganic coating prepared on the surface of the stent, and the drug is absorbed on the surface of the stent through the porous structure. The non-degradable polymer material may be Polymethacrylic Acids (PMMA) or Polystyrene-Isobutadiene-Styrene Copolymers (SIBS). The degradable polymeric carrier material may be Polylactic Acid (PLA) and copolymers thereof with other substances, such as copolymer PLGA thereof with glycolic acid, and copolymer PELA thereof with ethylene glycol.

Further, the surface of the substrate is distributed with grooves or micropores of 0.1 μm-10 μm.

The present invention further provides a preparation method of a medical instrument, comprising the following steps: preparing a micropowder or a solution containing amlexanox, and loading the drug onto a surface of the substrate through a dripping, filling or coating method.

Further, the coating method is one or more selected from ultrasonic atomization spraying, chemical vapor deposition, physical vapor deposition, ion beam spraying, dip-coating, micro spraying and brush coating.

Further, the spraying method is direct spraying, electrostatic spraying or anodic polarization spraying. The dip-coating method is direct dip-coating or electrode polarization dip-coating.

That is, the present invention is able to select a method of loading a drug on the surface of a substrate of the medical instrument to distribute amlexanox to the surface of the substrate of the medical instrument.

Further, a solvent used in the amlexanox solution is selected from the group consisting of paraffins, olefins, alcohols, aldehydes, amines, esters, ethers, ketones, aromatic hydrocarbons, hydrogenated hydrocarbons, terpene hydrocarbons, halogenated hydrocarbons, heterocyclic compounds, nitrogen-containing compounds, and sulfur-containing compounds.

Further, the solvent used in the solution containing amlexanox is one or more selected from ethyl acetate, n-propyl acetate, acetone, tetrahydrofuran, trichloromethane, and dichloromethane.

The present invention further provides a drug eluting stent, comprising: a stent body and an active substance or a pharmaceutical composition distributed on a surface of the stent body, wherein the active substance is amlexanox or a salt thereof, and the pharmaceutical composition comprises amlexanox or a salt thereof.

Further, the pharmaceutical composition further comprises an anti-proliferative drug.

Further, the drug-loading rate of the amlexanox on the drug eluting stent is 20 μg/cm$^2$-140 μg/cm$^2$.

Further, the anti-proliferative drug is selected from the group consisting of rapamycin, everolimus, tacrolimus, ridaforolimus, temsirolimus, zotarolimus, wortmannin, perifosine and idelalisib.

Further, the drug-loading mass ratio of the amlexanox to the anti-proliferative drug is (1:10)-(10:1), preferably (1:3)-(3:1), and most preferably (1:2.5)-(1.5:1).

The present invention inhibits the proliferation of smooth muscle cells of the vascular wall through the sustained release of amlexanox to the surface of the stent, promotes the re-endothelialization of the blood vessel and the healing of the injured vascular wall, prevents the occurrence of stent thrombosis, and reduces the time for patients to take anti-thrombotic and platelet drugs after surgery.

Further, the drug-loading way of the drug eluting stent is a carrier-free drug eluting stent.

The carrier-free drug eluting stent can be any carrier-free drug eluting stent which has been developed at present, and is mainly classified into a nanomicroporous preloading type, a stent beam surface crystallization preloading type, a stent beam surface roughening preloading type, and a microgroove/microvia preloading type. The specific implementations can refer to the prior art, such as the Janus stent produced by Sorin of Italy, the Yukon stent produced by Translumina of Germany, the BioFreedom stent produced by Biosensors of Singapore, the Dalian Yinyi stent, the Nano stent of the Beijing Lepu Medical Inc. and the like.

The material of the stent body may be a metal material or a polymer material.

The metal material may be a degradable or non-degradable metal material. The non-degradable material may be titanium, cobalt, tantalum, nickel-titanium alloy, nickel-titanium-niobium alloy, medical stainless steel, etc. The degradable alloy material is for example aluminum-magnesium alloy, so that complete biological degradation and absorption are able to be achieved.

The polymer material can also be classified into degradable or non-degradable materials, where the degradable material may be Polycaprolactone (PCL), Polyglycolic Acid (PGA), Poly-L-Lactic Acid (PLLA), Polycaprolactone Monoacrylate (PCLA), Polylactic Acid-Glycolic Acid (PLGA) copolymer, and the like.

Further, the material of the stent body is a biodegradable metal material and/or a biodegradable polymer material.

The carrier-free drug eluting stent is able to avoid the allergic and inflammatory reactions caused by the carrier and become the stent body after the drug is released, thus resulting in a low possibility of occurrence of late thrombosis and inflammation and a high safety. In the case of a fully degradable stent, the stent mechanically supports the vessel for a period of time after interventional operation and prevents restenosis by means of the eluted drug. The stent body then slowly degrades and is completely absorbed by the tissues. Thus, the probability of occurrence of late stent thrombosis is reduced, long-term antiplatelet therapy is not needed and no risk is existed in future.

The present invention has discovered a novel biological activity of amlexanox, which has a high activity of inhibiting the proliferation of smooth muscle cells, and has a low activity of inhibiting the growth of endothelial cells compared to the currently used smooth muscle cell proliferation inhibitors. It is especially suitable for medical instruments to prevent the occurrence of vascular RS without delaying endothelial repair. Therefore, it is able to shorten the time for patients to take antithrombotic and platelet drugs after surgery, and thus greatly improves the long-term efficacy.

DETAILED DESCRIPTION OF THE INVENTION

The technical solution of the present invention is further illustrated below in conjunction with specific embodiments. It should be understood that the embodiments are only intended to illustrate the present invention, and are not intended to limit the scope of the present invention. The experimental methods without indicating specific conditions in the following embodiments are generally carried out according to conventional conditions or according to the conditions recommended by the manufacturer, and the reagents without indicating the source in the following embodiments are commercially available.

The term "carrier" as used in the present invention, unless otherwise specified, refers to a pharmaceutically acceptable carrier which does not evanish the biological activity or property of the compound, and is relatively non-toxic, for example, giving a subject a certain substance would not cause undesired biological effects or detrimental interactions with any of the contained components.

The words "subject" or "patient" are used interchangeably herein to refer to an animal (including a human) that is acceptable for the treatment with the compounds and/or methods. "Subject" or "patient" is used herein to encompass both male and female genders unless specifically stated otherwise. Therefore, "subject" or "patient" includes any mammal, including but not limited to, human, non-human primates, such as mammals, dogs, cats, horses, sheep, pigs, cattle, etc., which is benefit from treatment with the compound. Animals suitable for treatment with the compounds and/or methods of the present invention are preferably human. In general, the terms "patient" and "subject" are used interchangeably herein.

As used herein, the "medical instrument" refers to an appliance, device or apparatus directly or indirectly used on a patient. The medical instrument involved in the present invention may be an instrument implanted in the body or an extracorporeal instrument. The instrument can be used temporarily or implanted permanently. The medical instrument involved in the present invention includes, but is not limited to, the following devices: stent, stent graft, synthetic patch, lead, electrode, needle, surgical instrument, angioplasty ball, wound drainage tube, shunt, tube, infusion sleeve, cannula, pellet, implant, blood oxygenation generator, pump, vascular graft, vascular access port, heart valve, annuloplasty ring, suture, surgical clip, surgical nail, pacemaker, nerve stimulator, orthopedic instrument, cerebrospinal fluid shunt, implantable drug pump, vertebral cage, artificial disc occluder, artificial blood vessel, drug-eluting balloon, and the like.

Embodiment 1: Cell Experiment

A. Drug Preparation:
  (I) Preparation of Amlexanox:
    a) Before the experiment, the drug stent loaded with amlexanox is placed into a Dimethyl Sulfoxide (DMSO) solution, completely dissolved, and further diluted to form a solution having a drug concentration of $10^{-2}$ mmol/ml;
    b) The drug solution having the drug concentration of $10^{-2}$ mmol/ml is diluted with DMSO to drug solutions having concentrations of $10^{-3}$, $10^{-4}$, $10^{-5}$, $10^{-6}$, $10^{-7}$, $10^{-8}$, $10^{-9}$ mmol/ml, respectively;

c) The prepared drug solutions with a series of concentrations are separately packaged, and then are stored at −20° C. for temporary storage;

d) When in use, the stored $10^{-2}$-$10^{-9}$ mmol/ml drug solutions diluted by the DMSO are taken out and restored to normal temperature. The drug solution of each concentration is diluted by 1,000 times with the corresponding complete cell culture medium for cell tests, that is, the final concentrations used are $10^{-5}$, $10^{-6}$, $10^{-7}$, $10^{-8}$, $10^{-9}$, $10^{-10}$, $10^{-11}$, $10^{-12}$ mmol/mL, respectively.

(II) Preparation of Rapamycin:

a) Before the experiment, the drug stent loaded with rapamycin is placed into the DMSO solution, completely dissolved, and further diluted to form a solution having a drug concentration of $10^{-2}$ mmol/ml;

b) The drug solution having the drug concentration of $10^{-2}$ mmol/ml is diluted with DMSO to drug solutions having the concentrations of $10^{-3}$, $10^{-4}$, $10^{-5}$, $10^{-6}$, $10^{-7}$, $10^{-8}$, $10^{-9}$ mmol/ml, respectively;

c) The prepared drug solutions with a series of concentrations are separately packaged, and then are stored at −20° C. for temporary storage.

d) When in use, the stored $10^{-2}$-$10^{-9}$ mmol/ml drug solutions diluted by the DMSO are taken out and restored to normal temperature. The drug solution of each concentration is diluted by 1,000 times with the corresponding complete cell culture medium for cell tests, that is, the final concentrations used are $10^{-5}$, $10^{-6}$, $10^{-7}$, $10^{-8}$, $10^{-9}$, $10^{-10}$, $10^{-11}$, $10^{-12}$ mmol/mL, respectively.

(III) Preparation of Combined Drug:

a) Before the experiment, the drug stent loaded with rapamycin and amlexanox (the molar ratio is 1:1) is placed into the DMSO solution, completely dissolved, and further diluted to form a solution having an amlexanox or rapamycin concentration of $10^{-2}$ mmol/ml;

b) The drug solution having the drug concentration of $10^{-2}$ mmol/ml is diluted with DMSO to drug solutions having the concentrations of $10^{-3}$, $10^{-4}$, $10^{-5}$, $10^{-6}$, $10^{-7}$, $10^{-8}$, $10^{-9}$ mmol/ml, respectively;

c) The prepared drug solutions of with a series of concentrations are separately packaged, and then are stored at −20° C. for temporary storage;

d) When in use, the stored $10^{-2}$-$10^{-9}$ mmol/ml drug solutions diluted by the DMSO are taken out and restored to normal temperature. The drug solution of each concentration is diluted by 1,000 times with the corresponding complete cell culture medium for cell tests, that is, the final concentrations used are $10^{-5}$, $10^{-6}$, $10^{-7}$, $10^{-8}$, $10^{-9}$, $10^{-10}$, $10^{-11}$, $10^{-12}$ mmol/mL, respectively.

B. In Vitro Cell Proliferation and Tests Thereof a) Selection of cell inoculation concentration: A 10 cells with good growing status and stable growth are selected. After the digestion, cell suspensions having the concentrations of $1\times10^4$/ml, $2\times10^4$/ml, $4\times10^4$/ml, $5\times10^4$/ml, and $10\times10^4$/ml are respectively prepared. The cell suspensions of the above concentrations are inoculated into a 96-well cell culture plate and cultured using the MTT colorimetry. Finally, the solution having a cell inoculation concentration exhibiting absorbance of 0.6-1.5 measured by a microplate reader at the wavelength of 570 nm is selected as the cell inoculation concentration for tests;

b) The suspension having the selected cell concentration is prepared to be inoculated into the 96-well cell culture plate;

c) The cell culture medium is absorbed, and the cell culture medium having the final concentration of drug is added. A drug-free cell culture medium is used as a blank control group, and a DMSO cell culture solution having the concentration of 1/1000 is used as a background control group. The cell culture medium is cultured for 72 hours in a cell incubator.

d) The MTT is added to culture for 4 hours, the cell culture medium on the culture plate is discarded, and the DMSO is added to dissolve for testing the absorbance.

C. Experimental Groups

The Human Aortic Smooth Muscle Cells (HASMCs) and Human Aortic Endothelial Cells (HAECs) are selected for experiments, and grouping is carried out according to drugs, each group implements 6 times of tests and the average result is as shown in Table 1, specifically as follows:

1. Control group: no addition of drugs;
2. Rapamycin group: the culture medium contains 1 μmol or 10 μmol of rapamycin;
3. Amlexanox group: the culture medium contains 1 μmol or 10 μmol of amlexanox; and
4. Rapamycin and amlexanox group: the culture medium contains 1 μmol or 10 μmol of rapamycin and amlexanox, respectively.

D. Experimental Results

The inhibition rates of smooth muscle cells and endothelial cells in each group of experiments are shown in Table 1 below.

TABLE 1

| Experimental groups | Smooth muscle cell inhibition rate (%) | Endothelial cell inhibition rate (%) |
|---|---|---|
| Control group | — | — |
| Rapamycin (1 μmol) | 9.1 | 7.7 |
| Amlexanox (1 μmol) | 11.6 | 0.9 |
| Rapamycin (6 μmol) | 18.9 | 16.0 |
| Amlexanox (6 μmol) | 19.0 | 2.8 |
| Rapamycin (10 μmol) | 22.5 | 21.8 |
| Amlexanox (10 μmol) | 23.4 | 3.5 |
| Rapamycin (1 μmol) + amlexanox (1 μmol) | 30.5 | 3.9 |
| Rapamycin (6 μmol) + amlexanox (6 μmol) | 35.4 | 5.7 |
| Rapamycin (10 μmol) + amlexanox (10 μmol) | 34.9 | 6.4 |

The inhibition rates of the smooth muscle cells and endothelial cells for the groups shown in Table 1 are based on the data of the control group.

As shown in Table 1, compared with rapamycin, the smooth muscle cell inhibition rate of amlexanox is slightly higher, and the endothelial cell inhibition rate of amlexanox is greatly reduced, showing a particularly prominent of the inhibitory selectivity. In addition, in the case of the combined use of amlexanox and rapamycin, a smooth muscle cell inhibition rate of more than 30% is able to be obtained at a low drug content, and the endothelial cell inhibition rate is greatly reduced compared to the inhibition rate of the single use of rapamycin. Moreover, the endothelial cell inhibition rate of the combination of amlexanox and rapamycin is not obviously increased, with the drug content increases.

Embodiment 2 Drug Eluting Stent 300 mg of amlexanox (drug) and 300 mg of PLGA (drug carrier) are mixed in 20 ml of chloroform. After the solute is completely dissolved, the solution is uniformly sprayed on the surface of the L605 cobalt-chromium alloy metal stent by ultrasonic atomization until the drug-loading rate reaches 50 μg/cm$^2$. The drug eluting stent is obtained after the solvent is completely volatilized at room temperature.

Embodiment 3 Nano-Microporous Preloading Type

Fine marks are formed on the surface of a stainless steel stent body through friction processing; the micronized amlexanox and the stent body are placed into a high-pressure sealing device; the device is activated to make the micronized drug particles embedded in the fine marks of the stent body; and the drug eluting stent is obtained after the drug-loading rate reaches 50 μg/cm$^2$.

Embodiment 4 Preparation Method of Grooved Drug Eluting Stent

First, a stent body is provided, and a groove is formed on the surface of the stent body for subsequent loading of the drug.

Next, amlexanox and a solvent are mixed to obtain a solution, where the solvent is selected from the group consisting of paraffins, olefins, alcohols, aldehydes, amines, esters, ethers, ketones, aromatic hydrocarbons, hydrogenated hydrocarbons, terpene hydrocarbons, halogenated hydrocarbons, heterocyclic compounds, nitrogen-containing compounds, and sulfur-containing compounds.

Then, the solution is loaded onto the stent body. Specifically, the solution is loaded in the groove on the surface of the stent body. The solution is loaded by: dripping or coating, and the coating includes one or more of ultrasonic atomization spraying, chemical vapor deposition, physical vapor deposition, ion beam spraying, dip coating, microspraying and brush coating.

Finally, the drug-loaded stent is obtained after the solvent is volatilized.

Embodiment 5 Animal Experiment

A. Research Subject:

Small male pigs aged 1-2 months are selected and fed with induced formula feed. Pigs with hyperglycemia, hyperinsulinemia, and early diabetic nephropathy such as microalbuminuria, urine sugar, and nephritis are selected as subjects.

B. Grouping

1. Rapamycin stent group: animals are implanted with the stent containing rapamycin (the rapamycin loading rate of the stent is 140 μg/cm$^2$);

2. Amlexanox stent group: animals are implanted with the stent containing amlexanox (the amlexanox loading rate of the stent is 140 μg/cm$^2$);

3. Rapamycin+amlexanox stent group 1: animals are implanted with the stent containing both rapamycin and amlexanox (the rapamycin loading rate and the amlexanox loading rate of the stent are 140 μg/cm$^2$ and 20 μg/cm$^2$, respectively);

4. Rapamycin+amlexanox stent group 2: animals are implanted with the stent containing both rapamycin and amlexanox (the rapamycin loading rate and the amlexanox loading rate of the stent are 140 μg/cm$^2$ and 70 μg/cm$^2$, respectively); and 5. Rapamycin+amlexanox stent group 3: animals are implanted with the stent containing both rapamycin and amlexanox (the rapamycin loading rate and the amlexanox loading rate of the stent are 140 μg/cm$^2$ and 140 μg/cm$^2$, respectively).

For the preparation of the above stent groups, please refer to Embodiment 4.

C. Stent Implantation

Aspirin and clopidogrel are administered daily starting three days before surgery. The animals are anesthetized before surgery, and are fixed with their backs on the operating table, then a venous access is established, a cannula is inserted in the trachea, and a ventilator is provided for assisting in breathing. The right femoral artery is punctured after coronary angiogram and local disinfection, a guide wire is delivered through a puncture needle, a 6F femoral artery sheath is delivered along the guide wire, and 150 Ukg of heparin is administered through the sheath. A 6F right coronary guiding catheter is delivered through the sheath to perform left and right coronary angiography. The target vessel selection avoids large vascular branches as much as possible. A balloon is swelled with a pressure pump in vitro to release the stent, and the balloon is retrieved after the stent is completely adhered to the wall and causes injury. The angiography is rechecked after surgery. The catheter is retrieved, the femoral artery sheath is drawn out, and the surgical site is locally pressurized to stop bleeding. The pigs are sent back to the pigpen after awake for feeding.

D. Experimental Results

The pigs are continuously fed for 45 days after the stent is implanted. The vascular intimal hyperplasia at the injury site is examined 45 days later. The thicknesses of the intima of the bleeding vessel implanted with the stent and media of the bleeding vessel implanted with the stent are assayed to calculate the FM ratio, and the results are shown in Table 2 below.

TABLE 2

| No. | Experimental groups | I/M |
|---|---|---|
| 1 | Rapamycin stent group | 0.553 ± 0.301 |
| 2 | Amlexanox stent group | 0.349 ± 0.160 |
| 3 | Rapamycin + amlexanox stent group 1 | 0.190 ± 0.104 |
| 4 | Rapamycin + amlexanox stent group 2 | 0.225 ± 0.133 |
| 5 | Rapamycin + amlexanox stent group 3 | 0.207 ± 0.089 |

It can be seen from the above results that the I/M of the combination of rapamycin and amlexanox is smaller than that of the single rapamycin or single amoxicillin, which indicates that the combination of rapamycin and amlexanox has a lower inhibition ratio over the intima in animals, and thus it is more conducive to rapid endothelialization of blood vessels.

Embodiment 6 Pharmaceutical Composition Eluting Stent

Amlexanox, paclitaxel and poly(styrene-b-isobutylene-b-styrene) triblock copolymer (SIBS) are respectively weighed in a weight ratio of 1:1:10 and mixed, and then added with tetrahydrofuran until a solid content percentage reaches 1%. A stent body having a groove is prepared, and the prepared solution is then injected into the groove by micro-spraying. The drug-loaded stent is obtained after being dried in vacuum for six hours to remove the tetrahydrofuran.

Embodiment 7 Drug-Loading Balloon

A drug balloon for treating vascular stenosis is prepared using a nylon balloon.

(1) The surface of the nylon balloon is pretreated for 30 minutes by low temperature plasma under nitrogen at −20° C. with the output power of 2,000 W, the frequency of 25 Hz, and the air pressure of 1 Pa;

(2) Polylysine is dissolved in ethanol to obtain a 60 mg/ml solution, the balloon flap obtained in step (1) is wound. The solution is dropwise coated to the balloon using a Hamilton MOD710SYR 100 μl NR syringe (DL Naturegene Life Sciences, Inc., China), and is dried naturally, so that a modified balloon is obtained;

(3) Amlexanox is dissolved in a mixed solution of DMSO/water (with the volume ratio of 70:30) to prepare a 15 mg/ml amlexanox solution. 400 mg of lysine is added to 10 ml of the above amlexanox solution and dissolved by stirring at 10 rpm. The solution is placed at −5° C. for 24 hours, and filtered to obtain a solid. The solid is dried at 40° C. for 60 minutes to obtain a drug crystal; and (4) The drug crystal obtained in step (3) is brushed onto the surface of the modified balloon obtained in step (2). The modified balloon is weighed and repeatedly brushed five times, dried at 60° C. under 1,000 Pa vacuum, flapped and wound, packaged and sterilized, so that the drug balloon is obtained.

It is assayed that the content of amlexanox in the prepared drug balloon is 345 μg.

Embodiment 8 Drug-Loading Balloon 500 mg of adhesive (such as PVP) is accurately weighed and dissolved in 10 mL of anhydrous ethanol, and stirred for 15 min for future use; 75 mg of amlexanox is dissolved in 10 ml of 50% ethanol solution and stirred for 15 min for future use. The adhesive solution is placed in a sample tube, and the balloon is immersed in the adhesive solution at a speed of 5 mm/s, and the balloon is pulled out at the rate of 2 mm/s after staying for 15 s. Then, the amlexanox solution is placed in another sample tube, and the balloon coated with the adhesive is treated five times in the same coating manner to obtain a drug loading balloon. The drug-loading rate is 200 μg/cm$^2$.

The technical solution provided by the present invention is able to inhibit the biological activity of proliferation of vascular smooth muscle cells without inhibiting the growth of the endothelial cell, namely providing a selective inhibitory effect. The technical solution provided by the present invention is able to prevent the incidence of vascular restenosis without delaying endothelial repair. Therefore, it is able to shorten the time for patients to take antithrombotic and platelet drugs after surgery, and thus greatly improves the long-term efficacy.

What is claimed is:

1. A drug stent, comprising a stent body and an active substance and a pharmaceutical composition distributed on a surface of the stent body, wherein the active substance or the pharmaceutical composition has an inhibitory action on smooth muscle cells without inhibiting a growth of endothelial cells, wherein the active substance is amlexanox or a salt thereof, and the pharmaceutical composition comprises rapamycin, wherein a drug-loading rate of each of amlexanox and rapamycin on the drug stent is from 1 μmol to 6 μmol and a drug-loading molar ratio of amlexanox to rapamycin is 1:1.

* * * * *